United States Patent [19]
Ko

[11] Patent Number: 6,127,168
[45] Date of Patent: Oct. 3, 2000

[54] CONTAINERS USEFUL FOR CELL CULTURES AND OTHER APPLICATIONS

[76] Inventor: Nan-Jing Ko, 13735 NW. 39th Ave., Gainesville, Fla. 32606

[21] Appl. No.: 09/199,226

[22] Filed: Nov. 24, 1998

[51] Int. Cl.[7] .................................................. C12M 1/14
[52] U.S. Cl. .................................. 435/299.1; 435/299.2; 435/304.1; 435/307.1; 422/102; 47/65.5; 47/65.7; 47/65.8; 383/104; 383/121.1
[58] Field of Search ............................. 435/299.1, 299.2, 435/304.1, 307.1; 422/102; 47/65.5, 65.7, 65.8; 383/104, 121.1

[56] References Cited

U.S. PATENT DOCUMENTS

| | | |
|---|---|---|
| 4,358,908 | 11/1982 | Song . |
| 4,890,757 | 1/1990 | Robbins, III . |
| 4,910,147 | 3/1990 | Bacehowski et al. . |
| 5,273,362 | 12/1993 | Buchanan ................................ 383/104 |
| 5,288,466 | 2/1994 | Burns . |
| 5,346,311 | 9/1994 | Siler et al. ................................ 383/75 |
| 5,464,097 | 11/1995 | Edwards et al. . |
| 5,468,638 | 11/1995 | Barker et al. . |
| 5,547,284 | 8/1996 | Imer ........................................ 383/104 |
| 5,681,742 | 10/1997 | MersKelly et al. . |
| 5,713,510 | 2/1998 | Walton . |

*Primary Examiner*—Leon B. Lankford, Jr.
*Attorney, Agent, or Firm*—Saliwanchik, Lloyd & Saliwanchik

[57] ABSTRACT

The subject invention provides inexpensive and convenient containers for holding a variety of substances. Although the containers of the subject invention are particularly well adapted for use in cell culture procedures, the versatile nature of these containers make them advantageous in a wide variety of applications.

14 Claims, 2 Drawing Sheets

CONTAINERS USEFUL FOR CELL CULTURES AND OTHER APPLICATIONS

BACKGROUND OF THE INVENTION

The present invention relates to new containers useful in a variety of applications. In a specific example, the containers can be used for growing cell cultures. These cells may be plant or animal cultures.

As the biotechnology, agricultural, and medical fields have advanced there has been an increasing need for growing cells in culture. The growth of cells in culture provides a controlled setting for growth of sensitive cells, genetically transformed cells, or other cells needing careful attention and/or a controlled environment.

Cell culture media is typically a solution of nutrients, amino acids, electrolytes, and/or vitamins. The solution may be supplemented with any of a large number of components including, for example, fetal bovine serum, which is believed to contain growth factors and other proteins that are essential to mammalian cell growth. Media is typically sold in either a liquid or powder form. If the media is sold in a powder form, it must be reconstituted prior to use.

Typically, liquid cell culture media is packaged and used in rigid bottles, or containers. Glass bottles are used to package the cell culture media because of their barrier properties. Because amino acids are readily oxidized an oxygen barrier is needed. Furthermore, a carbon dioxide barrier is needed because typically a bicarbonate buffer system is used in the media. Moreover, it is critical that the interior surface of the container is inert because of the sensitivities of the cells to toxic leachables.

In the growing of cell cultures, it is likely that the grower will want to provide various growth conditions at various stages of growth. Such conditions may include, for example, a condition under which the container is hermetically sealed, a condition under which the container is allowed to breathe only to a very limited extent, and a condition under which air is allowed to pass freely into and out of the closed container.

Researchers and commercial production facilities have used a variety of containers to grow cell cultures. For example, it is common for cell cultures to be grown in rigid plastic containers having a separate lid which screws or snaps onto the open top of the vessel. Alternatively, the open top of the vessel may be covered by a flexible plastic material such as parafilm. Sometimes test tubes or plastic or glass flasks are used to grow cell cultures. Typically, such test tubes or flasks will be fitted with an appropriate stopper such as a rubber stopper.

The process of utilizing rigid containers for cell culture procedures has some clear disadvantages. Of course, the storage of rigid containers utilizes a large amount of space. Prior to use, the bottles must be washed and sterilized. Moreover, when glass containers are used, there is a possibility that the bottles will break or be damaged during handling.

Additionally, the typical techniques of transferring tissue or cell cultures from container to container are time consuming and have a risk of contamination. Still a further disadvantage in using glass and plastic rigid bottles is that there is a problem of disposing of the container after it has been emptied. An additional disadvantage of using traditional containers is the cost associated with the handling of and the pre-filling processing of the containers.

A further disadvantage of using rigid reusable cell culture vessels is the time, effort, and expensive involved in washing and sterilizing these vessels. It is very important to avoid contamination in cell culture procedures and, therefore, it is critical to thoroughly clean and sterilize the vessels between uses. Such cleaning procedures are labor intensive and add to the cost of cell culture procedures.

Accordingly, there is a need for an improved container for containing cell culture media. Containers are also needed in a variety of other applications where it is desired to have an inexpensive, lightweight receptacle.

A principal object of the present invention is to provide an economical container which is easily used. Economy is not only present insofar as the cost of manufacture is concerned but also from the standpoint of efficient use of the area or space occupied by the containers. In the particular case of cell or tissue culture, an additional consideration for the grower is the problem of sterilizing the vessel and media between uses; the present invention overcomes this problem.

BRIEF SUMMARY OF THE INVENTION

The subject invention provides inexpensive and convenient containers for holding a variety of substances. Although the containers of the subject invention are particularly well adapted for use in cell culture procedures, the versatile nature of these containers makes them advantageous in a wide variety of applications.

In a preferred embodiment, the containers comprise a flexible bag having at its base one or more protrusions which allow the bag to remain upright when placed on a surface. The containers remain upright even when materials are placed in the container.

Although the containers of the subject invention can be washed and reused, they are relatively inexpensive and, therefore, can be disposed of after use thereby avoiding contamination and reducing labor costs associated with cleaning. Advantageously, the containers of the subject invention are lightweight, flexible, require very little room for storage, are easily used and can be disposed of easily without harm to the environment.

These containers, which can be closed to prevent the passage of air into the inside of the container, typically consist of a single piece construction and, therefore, do not have a separate top. These containers can be used in a variety of applications as described more fully herein.

In a preferred embodiment, the subject invention provides unique and advantageous containers for growing cells or tissue culture in vitro. In a specific embodiment, the subject invention relates to a new and improved cell culture container for supporting tissue cultures in a fluid medium containing nutrients which promote the cell culture growth. The containers of the subject invention are economical and easy to use. Also, because the containers are lightweight and inexpensive they are very advantageous for transporting cell culture materials. Thus, cell cultures can be transported short distances or even internationally in the containers in which they are grown.

In a further embodiment the subject invention pertains to methods of using the cell culture containers of the subject invention.

In yet further embodiments, the containers of the subject invention can be used to hold a variety of substances other than cell culture media. For example, the containers can be used to hold nursery plants for transplanting. Alternatively, the containers can be used to hold food items, such as, "finger foods" or sauces to facilitate convenience and cleanliness in the consumption of foods which are shared by multiple individuals. Additionally, the containers can be used to hold items that are intended to be disposed of such as, for example, seeds from fruits which have been consumed. In this embodiment, the containers of the subject invention can be reinforced around the circumference of the top of the container to add rigidity so that the container stays open widely for easy access.

Regardless of their intended use, the containers of the subject invention are highly advantageous because they are lightweight, convenient, disposable, easy to use, and do not require much space.

DETAILED DISCLOSURE OF THE INVENTION

The subject invention pertains to new and advantageous containers for use in a variety of applications. In a specific embodiment contemplated according to the subject invention, the containers described herein can be used in commercial or academic tissue or cell culture procedures.

Cell culture procedures are performed, for example, in agricultural research where new plants may be regenerated from cells of a mother plant. These procedures are also used to grow animal tissues starting from a small number of cells. Currently, rigid containers made of glass or rigid plastic are typically used in cell or tissue culture procedures. These containers typically have a separate top which is screwed or otherwise affixed to a bottom portion of the container. The prior art containers are cumbersome and typically require two hands to remove or replace the top. Containers which are currently used in cell culture procedures must be cleaned and sterilized between uses. This cleaning procedure is labor and energy intensive and adds significantly to the cost of tissue culture procedures. Furthermore, in accordance with current practice, cell cultures are often transferred prior to shipment so that the heavy and/or expensive containers, in which the cultures are initially grown, are not shipped. The current invention eliminates the need to transfer cell cultures prior to shipping.

Figure 1:
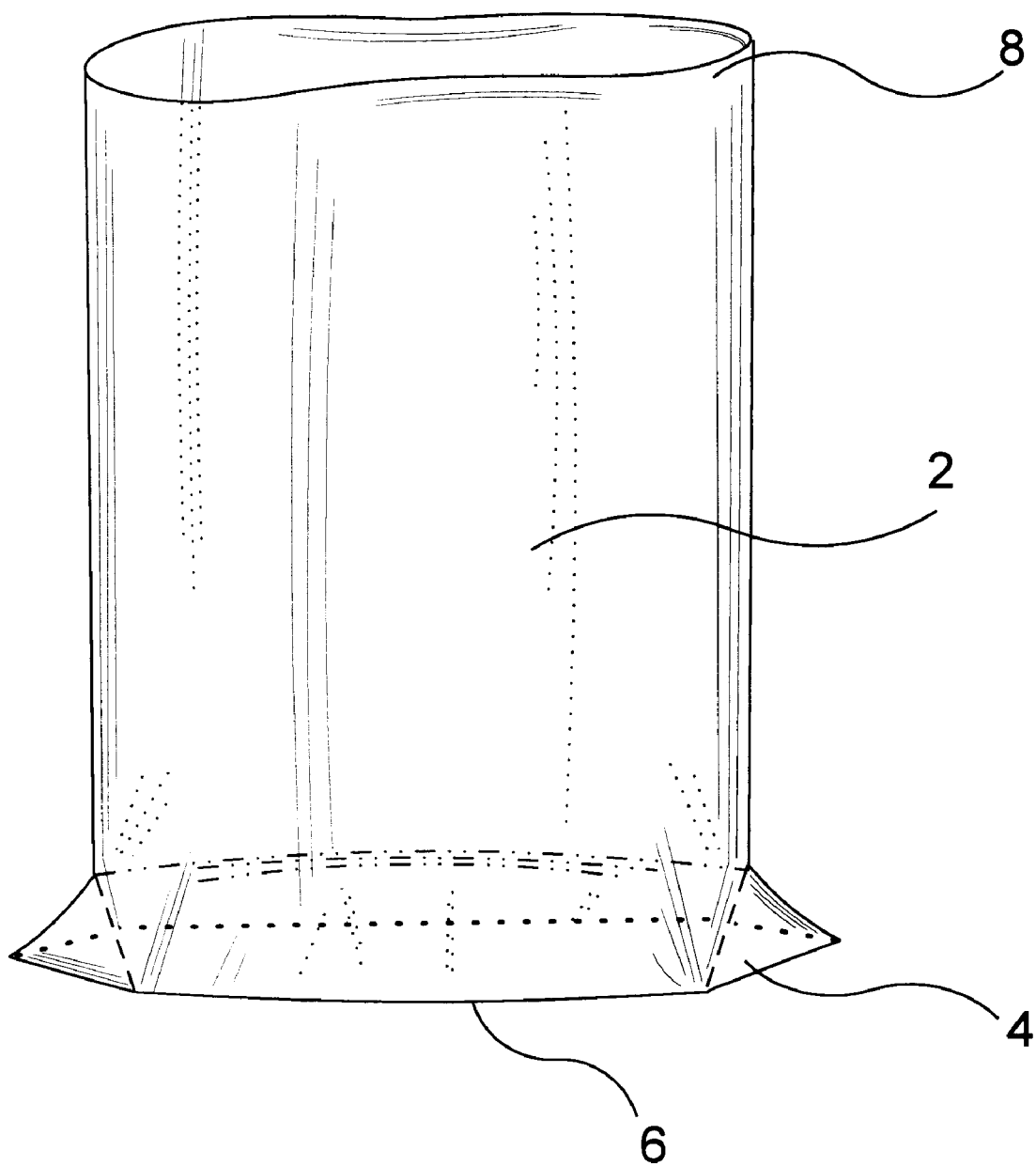
FIG. 1 shows one embodiment of the cell culture container of the subject invention.
Figure 2:
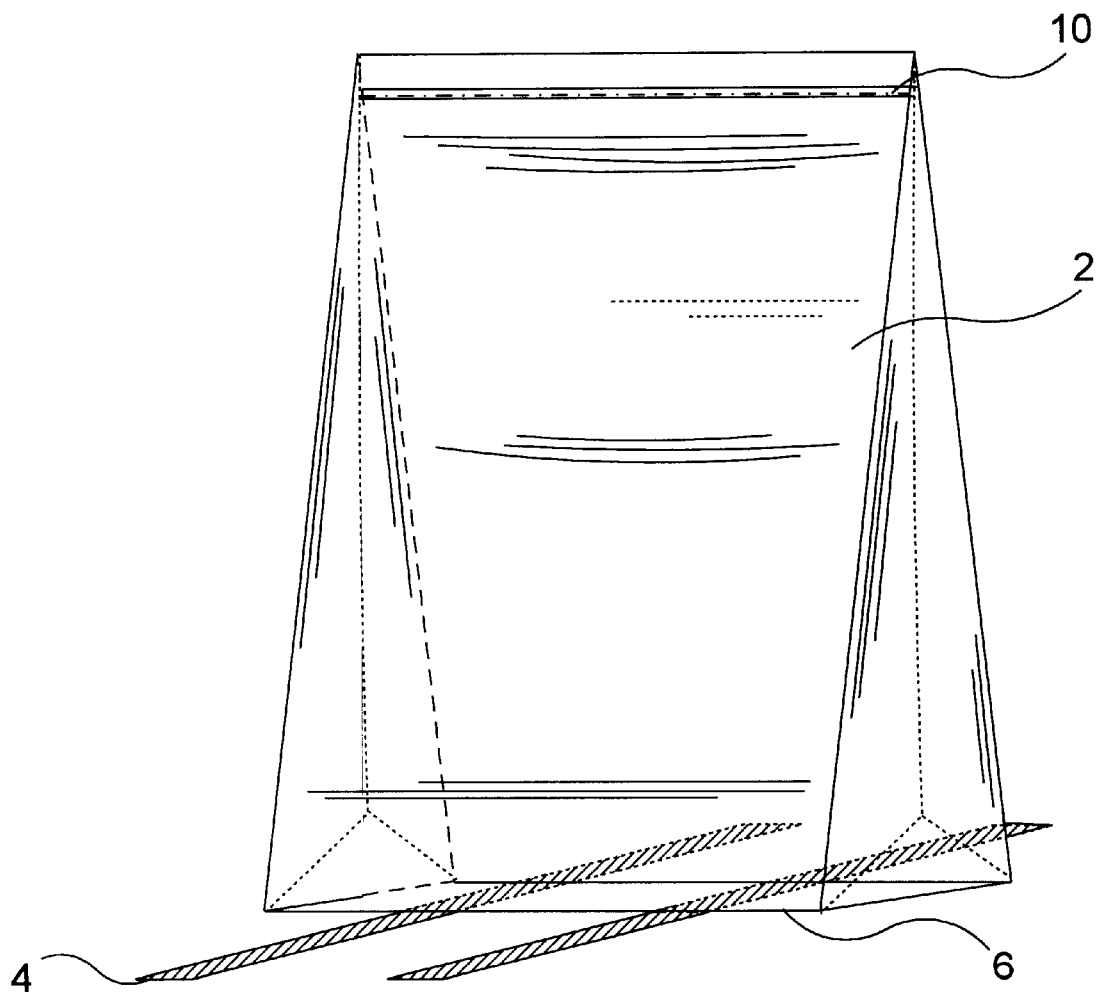
FIG. 2 shows a further embodiment of the cell culture containers of the subject invention.

In a preferred embodiment, the subject invention provides a new tissue or cell culture container. Specific embodiments of the cell culture containers of the subject invention are shown in FIGS. 1 and 2. The subject invention provides cell culture containers made from a non-rigid material which is impervious to water and air. The container typically comprises a closed bottom portion and a closeable open top portion such that the container has an internal space into which cell culture media can be placed. The closed bottom portion of the container comprises at least one protrusion which provides the container with stability such that the container does not tip over when the internal space contains cell culture media in sufficient quantities to establish a cell culture. In a specific embodiment, the container is essentially a flexible plastic bag 2 that has small projections 4 extending from the bottom portion 6 of the bag so that, when the plastic bag contains the liquid cell culture medium it will "stand up." Without the projections the plastic bag would typically fall over, spilling its contents.

The plastic bags of the subject invention can be made of any flexible material having sufficient strength and chemical properties to hold culture media. The material should be chemically and physically inert to culture media. As used herein, "non-rigid" and "flexible" refer to material without sufficient rigidity to remain upright in a stable position when filled with sufficient liquid cell culture media to facilitate the growth of cell cultures. For example, a container made of such "non-rigid" or "flexible" material, when filled about ¼ to ⅓ full with water would not stand upright stably and would readily tip over. The containers of the subject invention are made of a material which is essential impervious to water and air. The containers of the subject invention may be made, for example, from polymers or very lightweight, thin aluminum. In preferred embodiments, the containers are made from polypropylene or high density polyethylene (HDPE). High density polyethylene is particularly preferred. Although the bags of the subject invention are flexible and can be easily folded, the use of HDPE is preferred because it has sufficient structural integrity to enhance the stability of the bag so that an upright position can be maintained. Sterilization of a HDPE container has been found to enhance this structural integrity. Furthermore, HDPE can be disposed of readily through high temperature combustion thereby yielding environmentally inocous compounds which do not pose an environmental hazard.

The container of the subject invention can be easily closed by simply folding the top 8 of the container down. By making two or more folds it is possible to effectively prevent contamination. The container top can be held securely in the folded position by a paper clip or a similar device. The use of paper clips or similar securing devices is advantageous because they are inexpensive and easy to use. The fastening device may be re-used or disposed of. By folding the top of the bag multiple times it is possible to not only prevent air flow into or out of the bag but also to protect the top edge of the bag from contamination which could otherwise result from exposure to ambient air. This protection against contamination is important in cell culture procedures. The folding method for sealing the bags is also particularly advantageous when combined with the flexible nature of the bags because it is possible to clip multiple bags together with a single clip to conserve resources and space. In a further embodiment the container has a "zip-lock" top 10 or other similar means for sealing the top of the container to prevent air exchange and/or contamination.

The projections 4 which enable the container to remain upright when placed on a surface can be attached to, or part of, the base of the bag. The projections can be integrally molded with the bag, or attached through any suitable means. The projections must be of an appropriate size and shape to allow the bag, once filled with culture media, to remain upright on the intended surface. The projections which enable the container of the subject invention to stand upright typically will not have within the projections the material which is contained within the vessel. Thus, the projections are sealed off from the main compartment of the container. The projections may simply be an extended piece of the material from which the container is manufactured, or may include additional features which, for example, assist in maintaining the stability of the container. Such additional features can include, for example, an adhesive substance on the underside of the projection which causes the container to remain stabally attached to a surface upon which it is placed. The projections may also contain air, fluid, or a weighted substance to further increase stability.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A cell culture system comprising cell culture media and a cell culture container wherein said container is made from a non-rigid material having sufficient structural integrity to enhance stability and which is impervious to water and air and wherein said container comprises a closed bottom portion and a closeable open top portion such that said container has an internal space into which cell culture media can be placed; wherein said closed bottom portion comprises at least one protrusion which provides the container with stability such that said container does not tip over when said internal space contains cell culture media in sufficient quantities to establish a cell culture.

2. The cell culture container, according to claim 1, wherein said container is made from a material selected from the group consisting of plastic and lightweight aluminum.

3. The cell culture container, according to claim 2, wherein said container is made from a plastic selected from the group consisting of polypropylene and high density polyethylene.

4. The cell culture container, according to claim 1, wherein said container can be closed by folding the open top portion of said container.

5. The cell culture container, according to claim 1, wherein said closed bottom portion is oblong or rectangular in shape such that the oblong shape or rectangle has ends, wherein said protrusion extends from at least one end of the closed bottom portion of said container.

6. The cell culture container, according to claim 5, wherein said container comprises protrusions extending from each of two ends of the closed bottom portion of said container.

7. The cell culture container, according to claim 1, wherein said protrusions increase the surface area of contact between said container and a surface upon which said container is placed.

8. The cell culture container, according to claim 1, wherein said protrusion is integrally formed with said closed bottom portion of said container.

9. The cell culture container, according to claim 1, wherein said protrusion is fixedly attached to said bottom portion of said container.

10. The cell culture container, according to claim 1, wherein said protrusions have an internal s pace which can contain a substance having sufficient weight to increase the stability of said cell culture container.

11. The cell culture container, according to claim 10, wherein said internal space of said protrusion does not connect with the internal space of said container and, therefore, material placed into the container does not enter the internal space of said protrusion.

12. The cell culture container, according to claim 1, wherein said protrusion has an adhesive material to increase the stability of said container.

13. A method for growing cell cultures comprising adding cells to the cell culture container of claim 1 and culturing said cells.

14. The method, according to claim 13, wherein said cell cultures are transported in said cell culture containers.

* * * * *

UNITED STATES PATENT AND TRADEMARK OFFICE
CERTIFICATE OF CORRECTION

PATENT NO.    :    6,127,168

DATED         :    October 3, 2000

INVENTOR(S)   :    Jan-Jing Ko

It is certified that error appears in the above-identified patent and that said Letters Patent is hereby corrected as shown below:

Column 6, line 13: "internal s pace" should read --internal space--.

Column 6, line 26: "container" should read --system--.

Signed and Sealed this

Seventeenth Day of April, 2001

*Attest:*

NICHOLAS P. GODICI

*Attesting Officer*      *Acting Director of the United States Patent and Trademark Office*